United States Patent
Light, II et al.

(10) Patent No.: US 7,687,103 B2
(45) Date of Patent: Mar. 30, 2010

(54) COMPOSITIONS AND METHODS FOR PRESERVING PERMEATION LAYERS FOR USE ON ACTIVE ELECTRONIC MATRIX DEVICES

(75) Inventors: James P. Light, II, San Diego, CA (US); Kenny V. Nguyen, San Diego, CA (US)

(73) Assignee: Gamida for Life B.V., Rotterdam (NL)

( * ) Notice: Subject to any disclaimer, the term of this patent is extended or adjusted under 35 U.S.C. 154(b) by 0 days.

(21) Appl. No.: 11/846,187

(22) Filed: Aug. 28, 2007

(65) Prior Publication Data

US 2008/0069962 A1 Mar. 20, 2008

Related U.S. Application Data

(60) Provisional application No. 60/841,781, filed on Aug. 31, 2006.

(51) Int. Cl.
*B05D 5/00* (2006.01)
(52) U.S. Cl. .......................................... 427/58; 427/384
(58) Field of Classification Search ....................... None
See application file for complete search history.

(56) References Cited

U.S. PATENT DOCUMENTS

| | | | |
|---|---|---|---|
| 3,981,671 A | 9/1976 | Edwards | |
| RE30,130 E | 10/1979 | Edwards | |
| 4,205,028 A | 5/1980 | Brueggemann et al. | |
| 4,284,399 A | 8/1981 | Newcomb et al. | |
| 4,472,124 A | 9/1984 | Kashihara et al. | |
| 4,497,763 A | 2/1985 | Monnet | |
| 4,552,633 A | 11/1985 | Kumakura et al. | |
| 4,787,963 A | 11/1988 | MacConnell | |
| 4,897,228 A | 1/1990 | Miwa et al. | |
| 5,026,785 A | 6/1991 | Mage et al. | |
| 5,034,428 A | 7/1991 | Hoffman et al. | |
| 5,104,931 A | 4/1992 | Fleminger et al. | |
| 5,147,297 A | 9/1992 | Myers et al. | |
| 5,151,217 A | 9/1992 | Price | |
| 5,164,162 A | 11/1992 | Ridenour | |
| 5,171,782 A | 12/1992 | Candau et al. | |
| 5,173,147 A | 12/1992 | Shimoyama et al. | |
| 5,200,051 A | 4/1993 | Cozzette et al. | |

(Continued)

FOREIGN PATENT DOCUMENTS

DE 19705303 1/1998

(Continued)

OTHER PUBLICATIONS

Anderson, et al., "Polymerized Lyotropic Liquid Crystals As Contact Lens Materials", Physica A, 1991, 176, 151-167, Elsevier Science Publishers B.V. (North Holland).

(Continued)

*Primary Examiner*—Erma Cameron
(74) *Attorney, Agent, or Firm*—John P. White; Cooper & Dunham LLP

(57) ABSTRACT

An improved synthetic, polymer hydrogel permeation layer for use with an active electronic matrix device for biological assays. The permeation layer includes a dried coating of raffinose or a combination of raffinose and stachyose to protect the permeation layer from degradation during shipping and storage.

8 Claims, 2 Drawing Sheets

U.S. PATENT DOCUMENTS

| | | | |
|---|---|---|---|
| 5,212,050 A | 5/1993 | Mier et al. | |
| 5,217,492 A | 6/1993 | Guire et al. | |
| 5,238,613 A | 8/1993 | Anderson | |
| 5,244,799 A | 9/1993 | Anderson | |
| 5,334,310 A | 8/1994 | Frechet et al. | |
| 5,346,604 A * | 9/1994 | Van Sin et al. | 204/415 |
| 5,405,618 A | 4/1995 | Buttery et al. | |
| 5,445,934 A | 8/1995 | Fodor et al. | |
| 5,453,185 A | 9/1995 | Frechet et al. | |
| 5,460,872 A | 10/1995 | Wu et al. | |
| 5,478,893 A | 12/1995 | Ghosh et al. | |
| 5,491,097 A | 2/1996 | Ribi et al. | |
| 5,496,509 A | 3/1996 | Yamamoto et al. | |
| 5,510,074 A | 4/1996 | Rose | |
| 5,521,229 A | 5/1996 | Lu et al. | |
| 5,527,670 A | 6/1996 | Stanley | |
| 5,534,132 A | 7/1996 | Vreeke et al. | |
| 5,543,098 A | 8/1996 | Myers et al. | |
| 5,605,662 A | 2/1997 | Heller et al. | |
| 5,618,265 A | 4/1997 | Myers et al. | |
| 5,624,973 A | 4/1997 | Lu et al. | |
| 5,632,957 A | 5/1997 | Heller et al. | |
| 5,648,482 A | 7/1997 | Meyer | |
| 5,653,939 A | 8/1997 | Hollis et al. | |
| 5,667,667 A | 9/1997 | Southern | |
| 5,744,627 A | 4/1998 | Stowolitz et al. | |
| 5,763,503 A | 6/1998 | Cowperthwaite et al. | |
| 5,770,369 A | 6/1998 | Meade et al. | |
| 5,777,148 A | 7/1998 | Stowolitz et al. | |
| 5,783,054 A | 7/1998 | Raguse et al. | |
| 5,849,486 A | 12/1998 | Heller et al. | |
| 5,889,104 A | 3/1999 | Rosenmayer | |
| 5,919,523 A | 7/1999 | Sundberg et al. | |
| 5,929,208 A | 7/1999 | Heller et al. | |
| 5,952,398 A | 9/1999 | Dietz et al. | |
| 5,981,734 A | 11/1999 | Mirzabekov et al. | |
| 6,015,666 A | 1/2000 | Springer et al. | |
| 6,017,696 A | 1/2000 | Heller | |
| 6,031,277 A | 2/2000 | Sugiura et al. | |
| 6,039,897 A | 3/2000 | Lochhead et al. | |
| 6,048,690 A | 4/2000 | Heller et al. | |
| 6,051,380 A | 4/2000 | Sosnowski et al. | |
| 6,054,270 A | 4/2000 | Southern | |
| 6,064,461 A | 5/2000 | Nishida | |
| 6,066,448 A | 5/2000 | Wolfstadter et al. | |
| 6,093,302 A | 7/2000 | Montgomery | |
| 6,099,783 A | 8/2000 | Scranton et al. | |
| 6,099,805 A | 8/2000 | Hartlove | |
| 6,112,908 A | 9/2000 | Michaels | |
| 6,121,027 A | 9/2000 | Clapper et al. | |
| 6,121,489 A | 9/2000 | Dorner et al. | |
| 6,136,444 A | 10/2000 | Kon et al. | |
| 6,143,412 A | 11/2000 | Schueller et al. | |
| 6,197,145 B1 | 3/2001 | Todd et al. | |
| 6,197,881 B1 | 3/2001 | Cosnier et al. | |
| 6,245,249 B1 | 6/2001 | Yamada et al. | |
| 6,245,508 B1 | 6/2001 | Heller et al. | |
| 6,264,825 B1 | 7/2001 | Blackburn et al. | |
| 6,303,082 B1 | 10/2001 | John et al. | |
| 6,306,348 B1 | 10/2001 | Havens et al. | |
| 6,306,594 B1 | 10/2001 | Cozzette et al. | |
| 6,444,111 B1 | 9/2002 | Montgomery | |
| 6,458,547 B1 | 10/2002 | Bryan et al. | |
| 6,458,584 B1 | 10/2002 | Mirzabekov et al. | |
| 6,524,517 B1 | 2/2003 | Havens et al. | |
| 6,615,855 B2 | 9/2003 | Lopez et al. | |
| 6,673,433 B1 | 1/2004 | Saeki et al. | |
| 6,673,533 B1 | 1/2004 | Wohlstadter et al. | |
| 6,682,899 B2 | 1/2004 | Bryan et al. | |
| 6,689,473 B2 | 2/2004 | Guire et al. | |
| 6,733,643 B2 | 5/2004 | Matsumoto et al. | |
| 6,767,816 B2 | 7/2004 | Kleveland et al. | |
| 6,824,974 B2 | 11/2004 | Pisharody et al. | |
| 6,838,053 B2 | 1/2005 | Havens et al. | |
| 6,841,379 B2 | 1/2005 | Matson | |
| 6,960,298 B2 | 11/2005 | Krotz et al. | |
| 7,220,344 B2 | 5/2007 | Bentsen et al. | |
| 7,270,850 B2 | 9/2007 | Krotz et al. | |
| 2005/0123565 A1* | 6/2005 | Subramony et al. | 424/234.1 |
| 2005/0266456 A1 | 12/2005 | Williams et al. | |
| 2006/0105355 A1* | 5/2006 | Maurer | 435/6 |
| 2007/0034512 A1* | 2/2007 | Yamaoka et al. | 204/403.01 |

FOREIGN PATENT DOCUMENTS

| | | |
|---|---|---|
| EP | 0047645 B1 | 11/1984 |
| EP | 0226470 A2 | 6/1987 |
| EP | 0243501 A1 | 11/1987 |
| EP | 00446040 B1 | 11/1994 |
| JP | 59-227131 A | 12/1984 |
| WO | 93/22678 A2 | 11/1993 |
| WO | 96/07917 A1 | 3/1996 |

OTHER PUBLICATIONS

Antonietti, et al., "Polymerization in Microemulsions-A New Approach to Ultrafine, Highly Functionalized Polymer Dispersion", Macromol.Chem.Phys., 1995, 196, 441-446, Hülthig & Wepf Verlag, Zug.

Antonietti, et al., "Morphology Variation Of Porous Polymer Gels By Polymerization In Lytropic Surfactant Phases, Macromolecules", 1999, 32, 1383-1389, American Chemical Society.

Antonietti, et al., "Polymer Gels With a Micron-sized, Layer-Like Architecture by Polymerization in Lyotropic Cocogem Phases", Langmuir, 1998, 14, 2670-2676, American Chemical Society.

Antonietti, et al., "Synthesis Of Sponge-Like Polymer Dispersions Via Polymerization Of Bicontinuous Microemulsions", Colloid Polym Sci, 1996, 274, 696-702, Steinkopff Verlag.

Antonietti, et al., "Microemulsions Polymerization: New Surfactant Systems by Counterion Variation", Adv. Mater., 1996, 8, 10, 840-844, VCH Verlagsgellshaft mbH, Weinheim.

Arenkov, et al., "Protein Microchips: Use For Immunoassay & Enzymatic Reactions", Analytical Biochemistry, 2000, 278, 123-131, Academic Press.

Bates, "Polymer-Polymer Phase Behavior", Science, Feb. 22, 1991, 25, 898-905.

Benedicto, et al., "Bicontinuous Cubic Morphologies In Block Copolymers & Amphiphile/Water Systems: Mathematical Description Through The Minimal Surfaces, Macromolecules", 1997, 30, 3395-3402, American Chemical Society.

Brinker, et al., *Sol-Gel Science*, 1990, Academic Press, San Diego.

Brown, "Dot & Slot Blotting of DNA, Current Protocols in Molecular Biology", 1993, Supplement 21, 2.9.15-2.10.16.

Burban, et al "Organic Microporous Materials Made By Bicontinuous Microemulsion Polymerization", AlChE Journal, Apr. 1995, 41, 4, 907-914.

Chieng, et al., "Microporous Polymeric Materials By Microemulsion Polymerization: Effect of Surfactant Concentrations", Langmuir, 1995, 11, 3321-3326.

Chieng, et al., "Morphology Of Microporous Polymeric Materials By Polymerization Of Methyl Methacrylate & 2-Hydroxyethyl Methacrylate In Microemulsions", Polymer, 1995, 36, 10, 1941-1946, Elsevier Science Ltd, Great Britain.

Chieng, et al., "Formation of Microporous Polymeric Materials By Microemulsion Polymerization Of Methyl Methacrylate & 2-Hydroxyethyl Methacrylate", Journal of Applied Polymer Science, 1996, 60, 1561-1568, John Wiley & Sons, Inc.

Hentze, et al, "Synthesis Of Organic Polymer Gels In Microemulsions & Lyotropic Mesophases", Ber.Bunsenges. Phys. Chem., 1997, 101, 11, 1699-1702, Wiley-VCH, Weinheim.

Kempe, et al, "Receptor Binding Mimetics: A Novel Molecularly Imprinted Polymer", Tetrahedron Letters, 1995, 36, 20, 3563-3566.

Lee, et al., "Polymerization of Nonlamellar Lipid Assemblies", J. Am. Chem. Soc., 1995, 117, 5573-5578.

Lindblom, et al, "Cubic Phases & Isotropic Structures Formed by Membrane Lipids-Possible Biological Relevance", Biochimica et Biophysica Acta, 1989, 988, 221-256, Elsevier Science Publishers B.V. (Biomedical Div).

Liu, et al. "Effect of Non-Ionic Surfactants on the Formation of DNA/Emulsion Complexes and Emulsion-Mediated Gene Transfer", Pharmaceutical Research, vol. 13, No. 11, 1996, pp. 1642-1646.

O'Connell, et al, "Polyacrylamide Gels With Modified Cross-Linkages", Analytical Biochemistry, 1976, 76, 63-73, Academic Press, Inc.

Odian, *Principles of Polymerization*, 3$^{rd}$ Edition, (John Wiley & Sons: New York, New York), 1991, 232.

Ogawa, et al., "Preparation of Self-Standing Transparent Films of Silica-Surfactant Mesostructured Materials and the Conversion to Porous Films", Adv. Mater., vol. 10, No. 14, 1998, pp. 1077-1080.

Paul, et al., "Cubic Phase Polymer Hydrogels: Templated Polymerization from Surfactant Mesophases", AIChE Meeting, Dallas, Texas, Oct. 31-Nov. 5, 1999, 71.

Peters, et al., "Rigid Macroporous Polymer Monoliths", Adv. Mater, 1999, 11, 14, 1169-1181, Wiley-VCH, Weinheim.

ProZyme Streptavidin, Specification Sheets, http://www.prozyme.com/pdf/sa10.pdf, 6 pages.

Raj, et al., "Formation of Porous Polymeric Structures by the Polymerization Of Single-Phase Microemulsions Formulated with Methyl Methacrylate & Acrylic Acid", Langmuir, 1991, 7, 2586-2591, American Chemical Society.

Raj, et al. ,"Polymerization Of Microstructured Aqueous Systems Formed Using Methyl Methacrylate & Potassium Undeconoate", Langmuir, 1992, 8, 1931-1936.

Raj, et al., "Synthesis Of Porous Polymeric Membranes By Polymerization Of Micro-emulsions", Polymer, 1993, 34, 15, 3305-3312, Butterworth-Heinemann Ltd.

Raj, et al., "Microcellular Polymeric Materials From Microemulsions: Control Of Microstructure & Morphology", Journal Of Applied Polymer Science, 1993, 47, 499-511, John Wiley & Sons, Inc.

Righetti, et al., "On The Limiting Pore Size Of Hydrophilic Gels For Electrophoresis & Isoelectric Focusing", Journal Of Biochemical & Biophysical Methods, 1981, 4, 347-363.

Righetti, et al., "Towards New Formulations For Polyacrylamide Matrices, As Investigated By Capillary Zone Electrophoresis", Journal Of Chromatography, 1993, 638, 165-178, Elsevier Science Publishers B.V.

Rill, et al., "Templated Pores In Hydrogels For Improved Size Selectivity In Gel Permeation Chromatography", Analytical Chemistry, Jul. 1, 1998, 70, 13, 2433-2438.

Samal, et al., "Electroinitiated Polymerization Of Acrylamide In Acetonitrile Medium", J. Polym. Sci. Polym., 26, 1988, 1035-1049.

Sasthav, et al., "Characterization of Microporous Polymeric Materials: Pore Continuity & Size Distribution Via Thermal Analysis", Journal Of Colloid & Interface Science, Sep. 1992, 152, 2, 376-385.

Seddon, "Structure of the Inverted Hexagonal ($H_{11}$) Phase, & Non-Lamellar Phase Transitions Of Lipids", Biochimica et Biophysica Acta, 1990, 1031, 1-69, Elsevier Science Publishers BV (Biomedical Div).

Shiyakhtenko, et al., "Atomic Force Microscopy Imaging Of DNA Covalently Immobilized On A Functionalized Mica Substrate", Biophysical Journal , Jul. 1999, 77, 568-576, Biophysical Society.

Sigma-Aldrich Brij, 700 Specification Sheet, http://www/sigmaaldrich.com/catalog/search/SpecificationSheetPage/Aldrich/466387, 2007, 1 page.

Sosnowski et al., "Rapid Determination Of Single Base Mismatch Mutations In DNA Hybrids By Direct Electric Field Control", Proc. Natl. Acad. Sci. USA, Feb. 1997, 94, 1119-1123.

Srisiri, et al., 'Polymerization Of The Inverted Hexagonal Phase, J. Am. Chem. Soc., 1997, 119, 4866-4873, American Chemical Society.

Svec, et al., "Molded Rigid Monolithic Porous Polymers: An Inexpensive, Efficient & Versatile Alternative to Beads For The Design Of Materials For Numerous Applications", Ind. Eng. Chem. Res., 1999, 38, 34-48, American Chemical Society.

Vasiliskov, et al., "Fabrication Of Microarray Of Gel-Immobilized Compounds On A Chip By Copolymerization", BioTechniques, Sep. 1999, 27, 3, 592-605.

Viklund, et al., "Monolithic, 'Molded', Porous Materials With High Flow Characteristics For Separations, Catalysis, Or Solid-Phase Chemistry: Control Of Porous Properties During Polymerization", Chem. Mater., 1996, 8, 744-750, American Chemical Society.

\* cited by examiner

COMPOSITIONS AND METHODS FOR PRESERVING PERMEATION LAYERS FOR USE ON ACTIVE ELECTRONIC MATRIX DEVICES

RELATED APPLICATIONS

This patent application claims the priority benefit of U.S. Provisional Application Ser. No. 60/841,781, filed Aug. 31, 2006, the specification of which is incorporated herein by reference in its entirety.

FIELD OF THE INVENTION

The present invention provides improved synthetic polymer hydrogel permeation layers for use on active electronic matrix devices for biological assays. The hydrogel permeation layers incorporate a dried coating of raffinose or combination of raffinose and stachyose to protect the permeation layer from degradation, thereby increasing shelf-life and expanding permissible shipping and storage temperatures. Additionally, the present invention provides increased cartridge-to-cartridge and lot-to-lot consistency during fabrication. The present invention also provides a preservative method for synthetic polymer hydrogel permeation layers having copolymerized attachment sites for biomolecules of interest, such as nucleic acid probes.

BACKGROUND OF THE INVENTION

The following description provides a summary of information relevant to the present invention. It is not an admission that any of the information provided herein is prior art to the presently claimed invention, nor that any of the publications specifically or implicitly referenced are prior art to the invention.

By placing a plurality of nucleic acid probes on a surface, and exposing the surface to a sample containing target nucleic acids, many hybridization reactions may be carried out on a sample at the same time, simultaneously generating hybridization data for several target nucleic acids (the reverse dot-blot technique). Similarly, by immobilizing nucleic acids from several samples onto the surface, several samples may be probed with the same oligonucleotide probe at the same time (the dot-blot technique). Originally, dot-blot and reverse dot-blot hybridizations were carried out using nucleic acid probes crudely blotted onto a nucleic acid-binding membrane or filter. In the past few decades, several tools have been designed to place nucleic acid probes at defined locations in high densities on various types of surfaces (glass, polymers, silicon nitride, etc.) by methods such as physical deposition (e.g., ink-jet, microspray, pin deposition, microchannel deposition) or by in-situ polymerization techniques (e.g., photo-deprotection methods.) Such "microchip" based DNA arrays have been of great interest in recent years due to their enormous ability to facilitate rapid analysis of genetic information. Although very advanced techniques are utilized to generate these types of arrays, they still employ parallel hybridization of DNA to the immobilized capture probes in a passive mode. In other words, the nucleic acids present in the entire sample volume interact with the entire array surface at the same time, to the same extent.

In contrast, active electronic matrix arrays use an electric field to facilitate the rapid transport and hybridization of DNA on microchips. In general, active matrix array devices contain an array of electronically addressable microelectrodes on a substrate, which provide electric field control over a variety of biomolecular reactions including DNA transport, hybridization and denaturation. By using the electrodes to apply an electric field to a solution containing charged molecules, such as nucleic acids, the charge molecules can be rapidly transported to and concentrated at the electrodes which are biased opposite the charge of the molecules. This allows the transport of nucleic acid probes or amplicons to the microlocations in a very efficient and specific manner for binding to attachment moieties at the microlocations (a process sometimes referred to as "programming" the locations), allowing the generation of arrays for dot-blot or reverse dot-blot formats. After the probes or amplicons are immobilized at the microlocations, the electric field can again be used to rapidly direct the second hybridization assay component to the microlocation. Thus, electric field regulated hybridization is one to three orders of magnitude faster than passive hybridization under the same conditions, overcoming several of the limitations of passive hybridization.

These arrays, also known as active programmable electronic matrix devices, or APEX devices, have been extensively described, e.g. in U.S. Pat. Nos. 6,051,380 and 6,245,508, incorporated herein by reference in their entirety. In general, the devices comprise an array of individually controllable microelectrodes on a substrate, and optionally comprise additional counter electrodes for opposite biasing. The microelectrodes are overlaid by a thin permeation layer, defining the microlocations of the device above the microelectrodes. In addition to facilitating the attachment of biomolecules by providing a matrix to affix attachment moieties (e.g., streptavidin) the permeation layer separates the biomolecules from the electrode surface where hydrolysis and other potentially detrimental electrochemical reactions can occur. Although the permeation layer retards or prohibits the movement of the biomolecules towards the microelectrode, the permeation layer is sufficiently permeable to small molecules to permit ion exchange between the electrode surface and the buffer medium, allowing an electric current to flow. The active electronic matrix chips usually use electric current and voltage conditions wherein electric current densities are at least 0.04 nA/$\mu m^2$ (about 200 nA for an 80 μm diameter microlocation) and/or potentials sufficient to hydrolyze water. The electric current density is defined as the electric current divided by the area of the electrode used to support it.

Additionally, the effectiveness of the translocation of charged biomolecules such as nucleotide oligomers within an electronically-driven system such as an active electronic matrix chip depends on the generation of the proper gradient of positively and negatively charged electrochemical species by the anode and cathode, respectively. For example, effective nucleic acid (i.e. either DNA or RNA) transport may be accomplished by generation of protons and hydroxyl anions when the potential at the anode is greater than +1.29 V with respect to a "saturated calomel electrode" (SCE). The transport efficiency of charged molecules increases with increasing current density, thus driving the desire for operation at higher voltage drops and current densities and, thus, the need for evermore robust permeation layers.

The application of an electric current through the permeation layer has also been found to produce considerable chemical and mechanical stress on the thin permeation layer coating at the electrode surface. It has been found that when such thin layers are applied onto electrodes without a covalent attachment to the electrode surface, the permeation layer is prone to separate or "delaminate" from the electrode interface. It is believed this delamination is caused by a change in the chemical make-up at the interface between the permeation layer and the electrode resulting from the application of electronic potential at the electrode and by physical disruption from charged ions and gases emanating from the electrode. Thus, the permeation layer must have sufficient mechanical strength and be relatively chemically inert in order to withstand the rigors of changes at the electrode surface without inordinate stretching or decomposition.

Thus, the permeation layer of active electronic matrix devices is an important element in the overall function of the device. It must be sufficiently permeable to small aqueous ions, yet efficiently sequester biomolecules from the electrode surface. In addition, it must be able to withstand significant chemical and mechanical forces while maintaining its integrity and shape. Several materials have been utilized which provide these qualities. Agarose with glyoxal crosslinked streptavidin (SA) has been used as a permeation layer on commercially available, active electronic matrix chips, and the results of electronic hybridization of DNA on these chips has been reported in several publications (e.g., Sosnowski, et al., Proc. Nat. Acad. Sci. USA, 94:1119-1123 (1997), and Radtkey, et al., Nucl. Acids Resrch., 28(7) e17 (2000.))

Agarose is a naturally sourced carbohydrate polymer hydrogel, containing long polymer strands which are crosslinked by non-covalent bonding. Such hydrogels are referred to as "physical hydrogels," as they derive their structure from non-covalent interactions, as compared to "chemical hydrogels," which derive their structure from covalent bonds (or cross-links) between the polymer strands. Agarose permeation layers provide good relative fluorescent intensity measurements in nucleic acid assays such as hybridization assays for single nucleotide polymorphisms (SNPs) and short tandem repeat sequences (STRs) in amplicon and capture-sandwich formats, and also in primer-extension type nucleic acid assays which have been used for gene-expression analysis.

However, some disadvantages are encountered in the use of agarose as a permeation layer material. Both the manufacturing process and the fact that agarose is a naturally-sourced product introduce some variation, which may vary performance from batch to batch, necessitating stricter quality controls. This is not ideal for large-scale manufacturing. Thus, an alternative material which is not naturally derived, which can be easily formed into a permeation layer on the device, and which will meet or exceed the operating standard of agarose, is greatly desirable.

Polyacrylamide and other synthetic polymer gels offer an alternative to agarose hydrogel permeation layers. These materials are wholly synthetic, and thus offer strict quality control of the components. In addition, they may be easily molded onto the microelectrode array surface with a high degree of uniformity across the entire device. Permeation layers which are between 1 and 2 μm thick in the dry state can be easily produced in this manner, and are amendable to high-throughput manufacture. After molding, streptavidin is covalently linked to the surface of the hydrogel to provide attachment sites for biotinylated oligonucleotide probes or amplicons. Although traditionally formulated polyacrylamide hydrogels made by the micromolding process are uniform, and offer better product control, they do not perform as well as the agarose streptavidin permeation layers in most nucleic acid assays. Thus, there is still a need for high-performance synthetic polymer hydrogel permeation layers for use on active electronic matrix chip devices. Moreover, there is a need for a permeation layer and method for manufacturing same that preserves and protects the permeation layer from degradation over time, thereby extending the shelf-life and expanding the permissible storage and shipping temperatures for the cartridge containing the permeation layer.

SUMMARY OF THE INVENTION

The current invention provides a dried coating of raffinose or a combination of raffinose and stachyose that serves to preserve and protect the permeation layer from degradation, increase the shelf-life, and expand the permissible storage and shipping temperatures for cartridges containing permeation layers. In a preferred embodiment, a permeation layer having copolymerized attachment sites is preserved and protected through addition of a dried raffinose coating. In another preferred embodiment, a combination of raffinose and stachyose is dried onto the permeation layer.

In one embodiment, the raffinose or combination of raffinose and stachyose coatings are formed by dissolving the sugar up to 10% (w/v) in 0.05% Proclin in deionized water. The resulting sugar solutions are then dispensed onto the permeation layers so as to saturate the permeation layer and subsequently allowed to dry at ambient temperatures. The dried coating may be washed away with commonly used buffers or water when the permeation layer is ready for use.

In another embodiment, the present invention discloses a method of coating a permeation layer overlying an electrode on a substrate including the steps of preparing a permeation layer, which may include, for example, a hydrogel or a sol-gel, preparing a sugar-based preservative solution, covering the permeation layer with the preservative solution and allowing the preservative solution to dry on the permeation layer. In some embodiments, the sugar-based preservative solution contains up to about 10% raffinose, while in other embodiments, the preservative solution contains a mixture of raffinose and stachyose in an amount up to about 10% by weight. In certain embodiments, the sugar-based preservative solution contains about 5% raffinose and about 5% stachyose by weight; other embodiments use a sugar-based preservative solution having about 1% raffinose and about 9% stachyose. In still other embodiments, the sugar-based preservative solution has a concentration of about 0% raffinose and about 10% stachyose by weight.

DETAILED DESCRIPTION OF THE INVENTION

Figure 1:
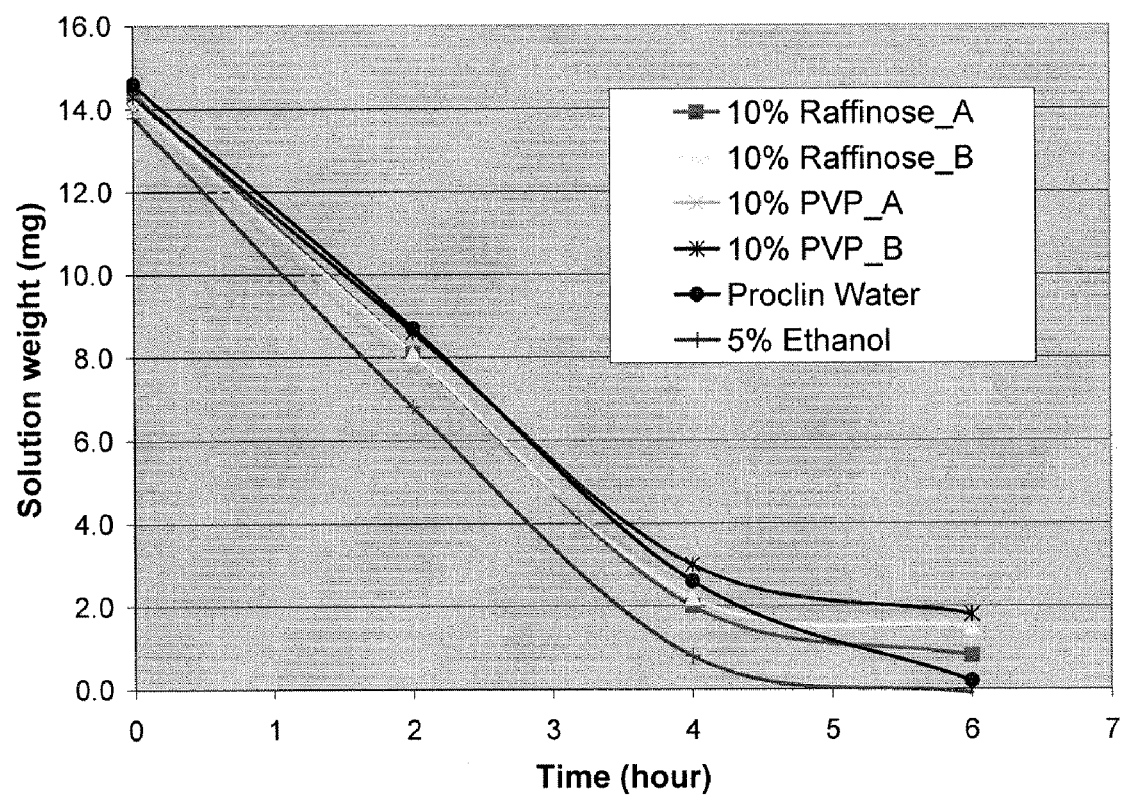
FIG. 1 is a chart showing a plot of the weight of various solutions as a function of the drying time.

As has been described, a key role in the function of active electronic matrix devices is played by the ion-permeable permeation layer which overlies the electrodes of the microlocations, or active sites, of these devices. As part of its function, the permeation layer provides attachment moieties for the attachment and immobilization of nucleic acids (or other specific binding entities, such as antibodies, or synthetic binding moieties such as pyranosyl-RNA). More importantly, the permeation layer separates the attached or tethered oligonucleotides and hybridized target DNA sequences from the highly reactive electrochemical environment generated immediately at the electrode surface. This highly reactive electrode surface, and the electrochemical products concentrated at the electrode surface, can rapidly destroy DNA probes and target DNA sequences which contact the surface or approach it too closely. Similar detrimental effects may be encountered with other macromolecular binding entities immobilized directly on the electrode surface. The permeation layer allows oligonucleotides and DNA fragments to be electronically concentrated above, rather than on, the electrode surface and hybridized to anchored complementary oligonucleotides while being protected from the reactive electrode surface and its immediate environment. The permeation layer also allows the gradual diffusion of the electrochemical reaction products ($H^+$, $OH^-$, gasses, etc.) into the solution around the microlocation, allowing these products to balance the charge through the permeation layer by ion exchange and to react with buffer species. Thus, the design of the microelectrode and permeation layer, forming a microlocation structure, allows high current densities to be achieved in a very confined area, while minimizing the adverse effects produced by the electrode itself.

Once specific binding entities, such as nucleic acids, have been addressed to microlocations and immobilized, the addressed devices are able to control and actively carry out a variety of assays and reactions. Analytes or reactants can be transported by free field electrophoresis to any specific microlocation where the analytes or reactants are effectively concentrated and reacted with the specific binding entity at the microlocation. The sensitivity for detecting a specific analyte or reactant in dilute sample solutions is improved because of this concentrating effect. An additional advantage, which also improved the specificity of the assays carried out on the device, is that any un-bound analytes or reactants can be removed by reversing the polarity of a microlocation (also known as "electronic washing".)

The ability to produce a precisely controlled high current level, or density, at individual microlocations even allows the selective "de-hybridization" of DNA fragments, achieving hybridization selectivity at the level of single base mismatches. Thus, the devices can further improve the specificity of assays and reactions by providing another parameter to encourage mismatch de-hybridization (along with the more traditional parameters of temperature and chemical environment), which is known as "electronic stringency", or "electronic stringency control (ESC)." For DNA hybridization reactions which require different stringency conditions, ESC overcomes an inherent limitation of conventional array technologies, which must rely on stringency conditions which are consistent for all sites over the entire array. The active devices of this invention can electronically produce different stringency conditions at each microlocation. This adds another controllable factor affecting hybridization, along with the more traditional factors such as temperature, salt concentration and the presence of chaotropic agents. Thus, all hybridizations can be carried out optimally in the same bulk solution, and multiple hybridization reactions can be carried out with minimal outside physical manipulations. Additionally, it may be unnecessary to change temperature in some cases, and the need for multiple washing procedures is greatly reduced.

Thus, the permeation layer of active electronic matrix devices is more than simply a mechanical support to hold attachment sites for specific binding entities. It is also an important factor in the overall performance and efficiency of the devices in their active electronic modes. Unlike coatings or gel supports which have been described for passive array devices, e.g., the gel-block arrays described in U.S. Pat. No. 5,770,721, which simply use hydrogel matrices as an attachment scaffold, permeation layers used on the active electronic matrix devices described herein must also allow the efficient active electronic transport of biomolecules to the microlocations of the device, and be conducive to electronic hybridization and/or stringency procedures.

As noted above, agarose hydrogels containing glyoxal-crosslinked streptavidin have proven to be effective permeation layer materials on active electronic matrix chip devices. In general, these permeation layer formulations have provided good mean fluorescence indices with minimal background. SNP assays run on the SA-agarose chips have demonstrated nearly 100% accuracy in several tests run with actual genomic samples, together with a high discrimination ratio for discerning between alleles in both homozygous and heterozygous samples. In addition, very good results have been obtained using SA-agarose active electronic matrix chips in STR and gene expression analysis assays.

However, as also described above, the use of SA-agarose as a permeation layer has several disadvantages in the manufacturing context. Agarose is a physical hydrogel, which derives its semi-solid structure from non-covalent interactions between long polysaccharide chains. As these interactions are temperature-dependent, changes in temperature change the viscosity of the agarose solution: at higher temperatures, the solution is more liquid, while it forms a solidified gel at room temperature. Thus, in order to coat the agarose permeation layer onto the active electronic matrix chip electrode array, the agarose solution must be kept at a relatively high and constant temperature during the manufacturing process. This also must be balanced with maintaining the activity of the streptavidin crosslinked to the agarose in the solution, which can denature if the temperature is too high. The current manufacturing method is to spin-coat the agarose solution onto the active electronic matrix chip surface. Thus, the agarose permeation layer production methods add significantly to the resources expended in producing the device.

Although this produces a fairly uniform thickness, submicron variations in thickness are often encountered when comparing the thickness of the permeation layer over microlocations on different sites on the chip. In addition, because agarose is a natural product, batch to batch variability may be seen with regard to its chemical characteristics and its performance as a permeation layer. This variability in both the materials and the manufacturing methods decreases the number of active electronic matrix chips which will meet quality control standards, also increasing the resources necessary to produce high-quality active electronic matrix chips with agarose-based permeation layers.

In contrast to the naturally-sourced physical hydrogels, such as agarose, synthetic polymer chemical hydrogels offer a more easily controlled quality and production characteristics. Synthetic polymer hydrogels are produced from individual monomeric components, which are usually synthesized themselves from basic organic chemical components. The monomers can be purified to very high quality, with identical physical and chemical characteristics between production batches. The monomeric components can be mixed in various formulas with cross-linker moieties and polymerized by a triggered initiator (e.g., by exposure of a photoinitiator to UV). Thus, chemical hydrogels offer strict control over the rate of polymerization and the characteristics of the resulting hydrogel, as compared the control afforded by physical hydrogels formed by pre-polymerized chains.

In addition, synthetic polymer hydrogels offer many advantages for mass production. They be easily molded onto the microelectrode array surface in situ with a high degree of uniformity across the entire device. Microreaction molds and methods of using them to form thin, uniform, synthetic polymer hydrogel layers on the surface of active electronic matrix chips have been described in WO 01/43938, Havens et al., incorporated herein by reference in its entirety. The microreaction molds disclosed comprise a mold cavity, with at least one side transparent to an electromagnetic radiation wavelength. In these systems, a small volume of the polymerization mixture (monomers, cross-linkers, and photoactivator) is placed into the mold cavity. The microelectrode array substrate is then pressed against the mold, forming an enclosed volume of the polymerization mixture on the substrate. The polymerization reaction is initiated by irradiating the enclosed volume with an appropriate wavelength of light for the photoinitiator (e.g., UV), and the polymerization reaction is allowed to proceed to completion. When the mold is removed, a thin, uniform, synthetic polymer hydrogel permeation layer has been formed on the microelectrode array.

Permeation layers which are between 1 and 2 μm thick, with sub-micron variations in thickness, can be easily produced in this manner, and are amendable to high-throughput manufacture. Multi-layer permeation layers (either overlaid or graft-polymerized onto the prior layers) be made in this manner as well, by using a series of molds with differing depths and/or widths. In addition, the molds can be designed to form individual permeation layers over each individual microelectrode, creating individually formed microlocations. In this manner, it is even possible to vary the permeation layer composition from microlocation to microlocation over the array of the active electronic matrix chip.

In the absence of stabilizers, cartridges containing permeation layers for use with the NanoChip™400 did not meet ideal shipping and storage requirements. For example, cartridges containing uncoated hydrogel permeation layers for use with Nanogen microarrays dehydrated and collapsed over time, thereby causing performance degradation. Surprisingly, it was found that addition of the sugar raffinose, alone or in combination with stachyose, to form a coating to the permeation layer resisted dessication and dramatically increased shelf-life and viability.

The present invention is not limited to a particular type of permeation layer. Indeed, permeation layers comprising hydrogels and sol-gels as exemplified in U.S. Pat. Nos. 6,303,082 and 6,960,298 may be used in conjunction with the preservatives and methods for preserving disclosed herein.

All patents, patent applications, and published patent applications, and other publications referred to herein are hereby incorporated herein in their entirety by reference, as if they were fully reproduced herein.

EXAMPLES

The invention will now be described in greater detail by reference to the following non-limiting examples regarding the production and use of preservatives applied to synthetic polymer hydrogel permeation layers for use on active electronic matrix devices.

Example 1

In this Example, several different preservative solutions were introduced onto APO-10 permeation layers on ACV400 Fcos prior to the cartridge assemble step to prolong APO-10 permeation layer shelf life.

A hydrogel solution was prepared and a batch of D1a ACV400 Fcos was molded. The Fcos with permeation layer was washed in 0.05% Proclin water for 1 hour with out stirring, then rinsed and dried with $N_2$. The preservative solutions shown in Table 1 were made and 20 μl of solution was pipetted into each Fcos flow-cell. The permeation layer was allowed to swell in the solutions for 20 minutes. The solutions were then pipetted out of the flow-cell and dried with $N_2$. The Fcos was stored in nitrogen-purged desiccators for about 72 hours. The Fcos permeation layers were assembled into cartridges. Finished cartridges were placed in 40° C. incubators for accelerated stability tests.

TABLE 1

Preservative Solutions

| Solution Number | Percent (W/V) Preservative Solution | Weight (mg) of Preservative Materials | Volume (μl) of Proclin water | Number of Fcos will be treated |
|---|---|---|---|---|
| 1 | 5% Trehalose | 53.7 | 1074 | 6 |
| 2 | 2.5% Trehalose, 2.5% Mannitol | 30 + 30 | 1200 | 6 |
| 3 | 2% Dextran | 18 | 900 | 6 |
| 4 | 2% Ficol 400 | 20.8 | 1040 | 6 |
| 5 | 2% PVP | 25.2 | 1260 | 6 |
| 6 | 2% PVP, 1% Trehalose | 24.9 + 12.5 | 1250 | 6 |
| 7 | 2% Dextran, 1% Trehalose | 20 + 10 | 1000 | 6 |
| 8 | 1% Trehalose | 10 | 1000 | 6 |

The cartridge lot number was A10254. There were 29 normal D1a (APO-10, 20 mg) cartridges and 41 cartridges treated with preservative solutions described in Table 1. The results are summarized in table 2 below.

TABLE 2

| Number on Pouch | Treatment Information | Number of good cartridges | Number of cart. Keep at 4° C. | Number of Cart. Test at 40° C. |
|---|---|---|---|---|
| #1 | 5% Trehalose | 5 | 1 | 4 |
| #2 | 2.5% Trehalose, 2.5% Mannitol | 6 | 1 | 5 |
| #3 | 2% Dextran | 6 | 1 | 5 |
| #4 | 2% Ficol 400 | 5 | 1 | 4 |
| #5 | 2% PVP | 4 | 1 | 3 |
| #6 | 2% PVP, 1% Trehalose | 4 | 1 | 3 |
| #7 | 2% Dextran, 1% Trehalose | 6 | 1 | 5 |
| #8 | 1% Trehalose | 5 | 1 | 4 |

There were 16 broken Fcos (out of 86) due to clamping issues arising during the cartridge assembly process. This particular lot of cartridges demonstrated unusual conductivties. Moreover, many of the cartridges had particulates on the surface of the permeation layers, regardless of what kind of preservative solutions were used.

Example 2

In this example, preservative sugar solutions were applied to APO-10 permeation layers on ACV400 Fcos prior to cartridge assembly stage to investigate prolonged permeation layer shelf-life.

A solution of 0.005% Proclin water was prepared by adding 1 g of Proclin 300 into 2 L of deionized water. The mixture was stirred for 10 minutes and filtered with a 0.2 μm bottle-top filter. A D1a hydrogel solution having the following mixing volume was made: 165 μl of monomer-detergent solution plus 110 μl modified Streptavidin and 30.6 μl 2% Darocur in DMSO. A batch of 75 Fcos was molded under the following conditions: UV=8.7 mW without OD filter (set/read=1120/1122 mW) with a compression of 165 mg. The batch was subsequently washed in a Petri-dish for one hour with Proclin water, then rinsed and dried with $N_2$.

The permeation layers were then treated with the preservative solutions described in Table 3.

TABLE 3

| Solution Number | Percent of Sugars in water (w/v) | Weight of sugars (mg) | Volume of Proclin water (ml) |
|---|---|---|---|
| #11 | 10% Trehalose | 111.4 | 1.114 |
| #12 | 5% Trehalose, 5% Mannitol | 50.2 + 49.9 | 1.000 |
| #13 | 10% Raffinose | 100.2 | 1.000 |
| #14 | 5% Trehalose, 5% Raffinose | 50.0 + 50.4 | 1.000 |
| #15 | 10% PVP | 100 | 1.000 |
| #16 | 5% PVP, 5% Trehalose | 50.5 + 50.1 | 1.000 |
| #17 | 5% PVP, 5% Raffinose | 49.9 + 50.1 | 1.000 |

Specifically, 15 µl of each preservative solution was transferred into each Fcos immediately after the Fcos were rinse and dried. There were 6 Fcos per solution. The treated Fcos were placed into 37° C. incubators for two hours before removal from the oven and storage in nitrogen desiccators until cartridges were assembled. Assembled cartridges were placed in a 40° C. incubator for the acceleration stability test.

The six Fcos that were treated with solution #12 did not have cracks, while the permeation layers treated with the other solutions did exhibit cracks.

Example 3

In this example preservative sugar solutions were introduced to APO-10 permeation layer on ACV400 Fcos prior to cartridge assembly step to prolong the permeation layer shelf-life. This experiment investigated 7 different preservative solutions, which were introduced to permeation layers that had dried for 24 hours dry as well as to permeation layers that had been immediately dried. The treated perm layers were held at 23° C. and 37° C. for drying.

A batch of permeation layers was molded using the following procedure: A solution of 0.005% Proclin water was prepared and filtered. Specifically, 9 mg of Darocur 4265 was added into 450 µl of DMSO to made 2% initiator solution. The D1a hydrogel solution was formulated with the following mixing volume: 165 µl of monomer detergent, 110 µl of modified streptavidin, and 30.6 µl of initiator solution. A batch of 59 Fcos was molded having the following variables: UV=8.6 mW without OD filter (set/read=1100/1122 mW/cm2), having a compression force=165 mg+/−15 mg. The molded Fcos were rinsed and washed in Petri-dishes for one hour, rinsed a second time, and dried with $N_2$. The finished Fcos were stored in refrigerator at 4° C. for 24 hours.

Preservative sugar solutions were made as described in table 4 below.

TABLE 4

| Solution Number | Percent of Sugar in water (w/v) | Weight of sugars (mg) | Volume of Proclin water (ml) |
|---|---|---|---|
| #11 | 10% Trehalose | 111.4 | 1.114 |
| #13 | 10% Raffinose | 100.2 | 1.000 |
| #15 | 10% PVP | 100.0 | 1.000 |
| #16 | 5% PVP, 5% Trehalose | 50.5 + 50.1 | 1.000 |
| #18 | 10% Trehalose, 2% Glycerol | 101.0 + 20 | 1.000 |
| #19 | 10% PVP, 2% Glycerol | 99.5 + 19.7 | 1.000 |

TABLE 4-continued

| Solution Number | Percent of Sugar in water (w/v) | Weight of sugars (mg) | Volume of Proclin water (ml) |
|---|---|---|---|
| #20 | 5% Trehalose, 5% PVP, 2% Glycerol | 50.2 + 49.8 + 20.4 | 1.000 |

Preservative solutions were added to permeation layers under the conditions described in table 5 below:

TABLE 5

| Fcos/cartridges Label | Permeation Conditions When Apply Sugar Sol. | Dry Temperatures |
|---|---|---|
| D-xx-23 | Dry permeation layers were stored at 4° C. for 24 hour | 23° C. |
| D-xx-37 | Dry permeation layers were stored at 4° C. for 24 hour | 37° C. |
| W-xx-23 | Re-hydrate in water for 1 hour, then dry with N2 | 23° C. |
| W-xx-37 | Re-hydrate in water for 1 hour, then dry with N2 | 37° C. |

The finished cartridges were labeled as indicated in the table above. The first letter refers to the condition of the permeation layer when the sugar solution was added. The two digit number in the middle refers to the sugar solution number. The last two digit number refers to the drying temperatures after the permeation layer was coated with the sugar solution.

For the D-xx-23 and D-xx-37 Fcos, 15 µl of preservative solutions were added in the dry permeation layers. Then, the sugar-coated Fcos was stored at 23° C. and 37° C. for 48 hours before transfer to cartridge assembly.

For the W-xx-23 and W-xx-37 Fcos, the permeation layers were re-hydrated in water for one hour and dried with nitrogen. After drying, sugar solutions were applied to the permeation layers and allowed to incubate at 23° C. or 37° C. for 48 hours. The re-hydration step was added to determine whether the cracking observed in some sugar-coated permeation layers was the result of polymer shrinkage during dehydration.

The table below shows the number of Fcos that were treated with different sugar solutions.

TABLE 6

| Sugar Solution # | D-23 | W-23 | D-37 | W-37 |
|---|---|---|---|---|
| #11 | 2 | 2 | 2 | 2 |
| #13 | 2 | 2 | 2 | 2 |
| #15 | 2 | 2 | 2 | 2 |
| #16 | 2 | 2 | 2 | 2 |
| #18 | 3 | 0 | 3 | 0 |
| #19 | 3 | 0 | 3 | 0 |
| #20 | 3 | 0 | 3 | 0 |

The treated Fcos were assembled into cartridges and held at 40° C. for accelerated stability study. The sugar-coated permeation layers were monitored over time for crystallization and cracking. For this experiment, most of the treated permeation layers were positive, as described in the following table.

TABLE 7

| Fcos ID | Number of Fcos | Observation after 24 hours | Observation after 48 hours | Number of Cartridges |
|---|---|---|---|---|
| D-11-23 | 2 | Good | Good | 2 |
| D-13-23 | 2 | Good | Good | 2 |
| D-15-23 | 2 | Good | Good | 2 |
| D-16-23 | 2 | Good | Good | 2 |
| D-18-23 | 3 | Good | Good | 3 |
| D-19-23 | 3 | Good | Good | 3 |
| D-20-23 | 3 | Good | Good | 3 |
| D-11-37 | 2 | Good | Good | 2 |
| D-13-37 | 2 | Good | Good | 2 |
| D-15-37 | 2 | Some small cracked lines at under fill area | Some small cracked lines at under fill area | 1 |
| D-16-37 | 2 | Some small cracked lines at under fill area | Some small cracked lines at under fill area | 0 |
| D-18-37 | 3 | Good | Good | 3 |
| D-19-37 | 3 | Good | Good | 3 |
| D-20-37 | 3 | Good | Good | 3 |
| W-11-23 | 2 | Good | Good | 1 |
| W-13-23 | 2 | Good | Good | 2 |
| W-15-23 | 2 | Good | Good | 0 |
| W-16-23 | 2 | Good | Good | 2 |
| W-11-37 | 2 | Good | Good | 2 |
| W-13-37 | 2 | Good | | 2 |
| W-15-37 | 2 | Some small cracked lines at under fill area | Some small cracked lines at under fill area | 2 |
| W-16-37 | 2 | Some small cracked lines at under fill area | Some small cracked lines at under fill area | 2 |

Example 4

In this experiment, the list of preservative materials was narrowed to two candidates, raffinose and PVP. In addition, add Triton X-100 and Ethanol were added to the sugar mixtures to accelerate the drying process and improve surface wettability.

A hydrogel solution was prepared. Two liters of 0.005% Proclin water were prepared and used to make preservative sugar solutions and wash the permeation layers. A 2% initiator solution was prepared by adding 11.5 mg of Darocur 4265 into 575 µl of DMSO. The final hydrogel solution was formulated with the following mixing volume: 165 µl of monomer detergent, 110 µl modified streptavidin and 30.6 µl initiator solution. The solution was filtered with 0.2 µm Millex LG syringe filter.

A mold station was set up using the following characteristics. UV intensity=8.8 mW/131 µw (open/close OD filter) (EXFO set/read=900/1071 mW). Compression force=175 mg+/−15. During the molding process, compression force fluctuated from Fcos to Fcos. The force was anywhere from 139 mg to 217 mg, which was unusual. Polymerization time was 30 second without OD filter.

The molded Fcos were rinsed with 0.005% Proclin water for five seconds each using a squirt bottle. The Fcos were soaked in large Petri-dish with Proclin water for one hour and rinsed again with Proclin water. The Fcos were then dried with $N_2$ and inspected before treatment with preservative sugar solutions.

The molded Fcos were treated with different preservative solutions as in the table below.

TABLE 8

| Solution Number | Solution Information | Good Fcos | Rejected Fcos | Total Treated Fcos |
|---|---|---|---|---|
| #13 | 10% (w/v) Raffinose | 14 | 6 | 20 |
| #15 | 10% (w/v) PVP | 10 | 5 | 15 |
| #21 | 10% (w/v) Raffinose in 5% (v/v) Ethanol | 4 | 4 | 8 |
| #22 | 10% (w/v) PVP in 5% (w/v) Ethanol | 4 | 4 | 8 |
| #0 | No Treatment | 9 | 0 | 9 |

A total of 15 µl of sugar solution was dispended onto each Fcos, which were then stored in closed Petri-dishs, 10 Fcos each, at room condition for 64 hours. The dried Fcos were visually inspected and transferred to cartridge assembly. During the cartridge assembly process, the Fcos were kept at room condition. After the cartridges were assembled, they were inspected again and viewed under a confocal microscope. The cartridges were stored at different temperatures for stability study.

The results are summarized in the following table.

TABLE 9

| Solution Number | Mixture Information | Comment on Issues |
|---|---|---|
| #23 | 10% Raffinose with 25 µl dispensing volume | 25 µl dispensing volume is larger than the Fcos flow cell volume. Thus, solution spread out to ceramic surface. |
| #24 | 10% PVP with 25 µl dispensing volume | 25 µl dispensing volume is larger than the Fcos flow cell volume. Thus, solution spread out to ceramic surface. |
| #25 | 10% Raffinose with 0.05% Triton X-100 | There are no improvement on surface wettability |
| #26 | 10% PVP with 0.05% Triton X-100 | There are no improvement on surface wettability |
| #27a | 10% Raffinose in 50% Ethanol | Very hard to dissolve and have many cracked lines when solution is dry |
| #27b | 10% Raffinose in 75% Ethanol | Raffinose does not dissolve |
| #27c | 10% Raffinose in 100 Ethanol | Raffinose does not dissolve |
| #28a | 10% PVP in 50% Ethanol | Many cracked lines when the solution are dry |
| #28b | 10% PVP in 75% Ethanol | Many cracked lines when the solution is dry |
| #28c | 10% PVP in 100% Ethanol | Many cracked lines when the solution is dry |

Assembled and treated cartridges were stored at various conditions, as shown in the following table.

TABLE 10

| Storage Temperature | Treated with #13 Solution | Treated with #15 Solution | Treated with #21 Solution | Treated with #22 Solution | Untreated (D1a) |
|---|---|---|---|---|---|
| 4° C. | 3 (13O, 13P, and 13Q) | 3 (15H, 15I, and 15J) | 2 (21D and 21E) | 3 (22E, 22F, and 22G) | 8 |
| 40° C. | 12 (13D to 13N) | 4 (15D to 15G) | 3 (21A, 21B, and 21C) | 4 (22A to 22D) | 0 |
| 55° C. | 3 (13A, 13B, and 13C) | 3 (15A, 15B, and 15C) | 0 | 0 | 0 |

In general, PVP-treated permeation layers appear to crack when stored at room temperature or higher. Raffinose treated cartridges were more stable. All of the cartridges stored at 55° C. for 13 days were cracked.

Example 5

In this example, the time it takes for the sugar coated layer to dry before transfer the Fcos to cartridge assembly process was determined.

The evaporation rate of the sugar solutions was determined. Six empty ACV400 Fcos (with no perm layer) were used. The weight of the Fcos was recorded before and after 15 μl of solution was dispended and evenly spread out onto the Fcos' flow-cell. Each of the Fcos were stored in a large Petri-dish with the lid closed. The Petri-dish was placed on lab bench at normal room condition (humidity was about 40+/−10). The weights of the Fcos were measured over time to determine the evaporation rate of the solution. The solutions used for this study were water, 5% ethanol, 10% Raffinose, and 10% PVP.

The weight of the solutions was calculated and plotted it as a function of drying time. The slope of the linear fit line on graph 2 provides the average evaporation rate of the solutions. The calculated dry time is 4.7 hours. As shown in the graph below, the 5% ethanol curve has a slightly steeper slope, indicating that the ethanol solution vaporizes faster than water and sugar solutions.

The end values of all the sugar solution curves at the 6 hour point were slightly higher than the water and ethanol, indicating that about 10% of the materials were left over after the water completely evaporated.

TABLE 11

| Fcos Number | Test Solution | Weight of Fcos (mg) | Fcos & Solution (mg) | After 2 hours (mg) | After 4 hours (mg) | After 6 hours (mg) |
|---|---|---|---|---|---|---|
| 1 | 10% Raffinose | 771.9 | 786.3 | 780.0 | 773.9 | 772.7 |
| 2 | 10% Raffinose | 780.7 | 794.9 | 788.8 | 782.9 | 782.2 |
| 3 | 10% PVP | 804.5 | 818.5 | 812.2 | 807.0 | 806.3 |
| 4 | 10% PVP | 810.6 | 824.9 | 819.2 | 813.6 | 812.4 |
| 5 | H2O | 807.6 | 822.2 | 816.3 | 810.2 | 807.8 |
| 6 | 5% Ethanol | 820.6 | 834.4 | 827.4 | 821.4 | 820.5 |

TABLE 12

| | 0 hour | 2 hours | 4 hours | 6 hours |
|---|---|---|---|---|
| 10% Raffinose_A | 14.4 | 8.1 | 2.0 | 0.8 |
| 10% Raffinose_B | 14.2 | 8.1 | 2.2 | 1.5 |
| 10% PVP_A | 14.0 | 7.7 | 2.5 | 1.8 |
| 10% PVP_B | 14.3 | 8.6 | 3.0 | 1.8 |
| Proclin Water | 14.6 | 8.7 | 2.6 | 0.2 |
| 5% Ethanol | 13.8 | 6.8 | 0.8 | −0.1* |
| Average | 14.2 | 8.0 | 2.2 | 1.0 |
| Stdv. | 0.3 | 0.7 | 0.8 | 0.8 |

Figure 2:
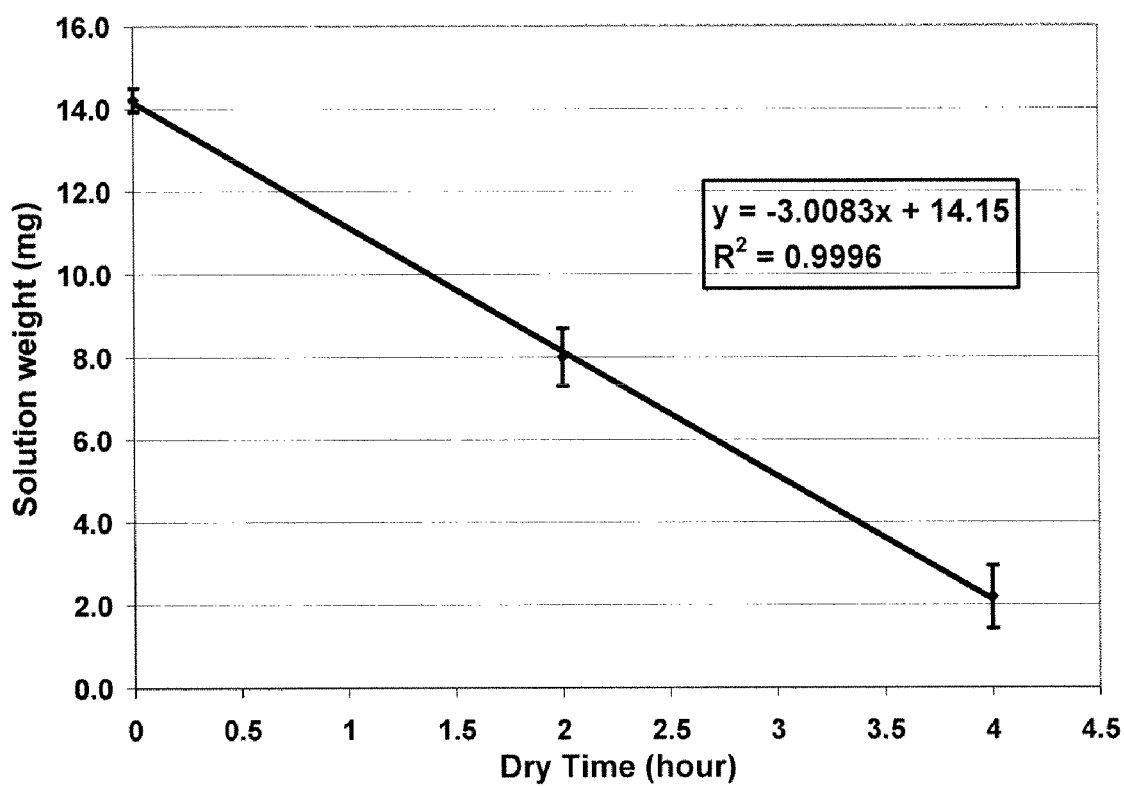
FIG. 2 is a chart showing a plot of the average evaporation rate of various solutions.

Based on the information provided in Table 11, the weight of the solutions was plotted as a function of drying time as shown in FIG. 1. The 5% ethanol curve had a slightly steeper slope than the other curves, indicating that the ethanol solution evaporates quicker than the water and sugar solutions. The end values of all the sugar solutions curves at 6 hours were slightly higher than water and ethanol indicating that about 10% of the material remained after the water completely evaporated. FIG. 2 shows the slope of a linear fit line demonstrating the average evaporation rate of the solutions. The calculated drying time was 4.7 hours.

Example 6

In this experiment, stachyose was added to the raffinose preservative solutions to determine whether such an addition would alleviate cracking in the permeation layers.

Solutions of 10% raffinose and 10% stachyose were prepared. The 10% stachyose solution was made by dissolving 300 mg of stachyose hydrate powder onto 2.7 ml of 0.05% Proclin 300 solution. Test solutions were prepared by mixing the 10% Raffinose and 10% Stachyose solutions together at different volume ratios. A total of six mixtures were made as shown in the table below.

TABLE 13

| Solution ID | Amount of 10% Raffinose Solution (μl) | Amount of 10% Stachyose Solution (μl) | Final Volume (μl) | Percent of Raffinose in The Mixture | Percent of Stachyose in The Mixture | Comment |
|---|---|---|---|---|---|---|
| Solution 0 | 1000 | 0 | 1000 | 10% | 0% | Control solution |
| Solution 1 | 900 | 100 | 1000 | 9% | 1% | |
| Solution 2 | 500 | 500 | 1000 | 5% | 5% | |
| Solution 3 | 100 | 900 | 1000 | 1% | 9% | |
| Solution 4 | 0 | 1000 | 1000 | 0% | 10% | |
| Solution 5 | 950 | 50 | 1000 | 9.5% | 0.5% | |

Crystallization Test on Cover Glasses

The test solutions were pipetted onto cover glasses, 15 μl of solution per glass, and allowed to incubate at room temperature in large Petri-dishes to evaporate. For each solution, sixty cover glasses were used. Ten out of the sixty test samples were added with a very small amount of raffinose powder to catalyze crystallization of the solution.

The results showed that all of the 50 evaporation samples of each test solution did not crystallize, thereby demonstrating that slow evaporation of the solutions at room conditions was not the cause of the crystallization. However, during the evaporation period, some of the 10 test samples containing additional raffinose powder crystallized, suggesting that when non-solvent materials are introduced into the system, supersaturation of the sugar solutions may occur and induce cracking. Thus, solutions containing stachyose or solutions having reduced concentrations of raffinose decrease the chance of the sugar solutions reaching super saturated levels and crystallizing.

Example 7

In this hold time study, 10% Raffinose treated H4 hydrogel molded NanoChip® 400 FCOS were held for 11 days, as opposed to the standard overnight period. After 11 days, the FCOS were inspected under microscope, assembled into cartridges and subjected to FV QC assay test.

All of the FCOS were inspected under a microscope and appeared to be normal after 11 days of storage at ambient conditions. The room temperature and relative humidity were recorded as shown below.

TABLE 14

|   | Date | Room Temperature | Room Humidity Range |
|---|---|---|---|
| 1 | Jul. 29, 2005 | 68.5° F. | 47%-75% |
| 2 | Jul. 30, 2005 | 67.0° F. | 50%-74% |
| 3 | Jul. 31, 2005 | 68.0° F. | 48%-75% |
| 4 | Aug. 01, 2005 | 68.2° F. | 47%-75% |
| 5 | Aug. 02, 2005 | 68.0° F. | 47%-72% |
| 6 | Aug. 03, 2005 | 68.5° F. | 47%-73% |
| 7 | Aug. 04, 2005 | 68.9° F. | 46%-70% |
| 8 | Aug. 05, 2005 | 68.4° F. | 47%-74% |
| 9 | Aug. 06, 2005 | 68.5° F. | 50%-74% |
| 10 | Aug. 07, 2005 | 68.0° F. | 50%-76% |
| 11 | Aug. 09, 2005 | 68.7° F. | 47%-74% |

Modifications and other embodiments of the invention will be apparent to those skilled in the art to which this invention relates having the benefit of the foregoing teachings, descriptions, and associated drawings. The present invention is therefore not to be limited to the specific embodiments disclosed but is to include modifications and other embodiments which are within the scope of the appended claims. All references are herein incorporated by reference.

We claim:

1. A sugar-based coating for a permeation layer overlying an electrode on a substrate, the coating comprising a solution of raffinose and stachyose in combination.

2. The sugar-based coating of claim 1, wherein the solution of raffinose and stachyose further comprises raffinose and stachyose in combination in an amount of between about 0.5% by weight to about 10% by weight, and wherein the permeation layer comprises a material selected from the group consisting of hydrogels and sol-gels.

3. A method of coating a permeation layer overlying an electrode on a substrate, the method comprising the steps of:
   a. preparing a permeation layer
   b. preparing a sugar-based preservative solution comprising raffinose and stachyose in combination in an amount of between about 0.5% by weight to about 10% by weight;
   c. covering the permeation layer with an amount of preservative solution sufficient to substantially cover an outside surface of the permeation layer; and
   d. allowing preservative solution to dry on the permeation layer,
   wherein the permeation layer comprises a material selected from the group consisting of hydrogels and sol-gels.

4. The method of claim 3, wherein the sugar-based preservative solution comprises about 5% raffinose by weight and about 5% stachyose by weight.

5. The method of claim 3, wherein the sugar-based preservative solution comprises about 9% raffinose by weight and about 1% stachyose by weight.

6. The method of claim 3, wherein the sugar-based preservative solution comprises about 0% raffinose by weight and about 10% stachyose by weight.

7. A sugar-based coating for a permeation layer overlying an electrode on a substrate, the coating comprising a solution of stachyose.

8. The sugar-based coating of claim 7, wherein the solution of stachyose further comprises stachyose in an amount of between about 0.5% by weight to about 10% by weight.

* * * * *